(12) United States Patent
Nagao et al.

(10) Patent No.: US 7,547,803 B2
(45) Date of Patent: Jun. 16, 2009

(54) PROCESS FOR PRODUCING A HIGH PURITY AROMATIC POLYCARBOXYLIC ACID

(75) Inventors: Shinichi Nagao, Okayama (JP); Masato Inari, Okayama (JP); Jitsuo Oishi, Okayama (JP); Kenji Nakaya, Okayama (JP); Hiroshi Machida, Okayama (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 385 days.

(21) Appl. No.: 10/861,497

(22) Filed: Jun. 7, 2004

(65) Prior Publication Data

US 2004/0260052 A1     Dec. 23, 2004

(30) Foreign Application Priority Data

Jun. 20, 2003     (JP) .............................. 2003-176294

(51) Int. Cl.
C07C 51/42     (2006.01)
(52) U.S. Cl. ...................................................... 562/485
(58) Field of Classification Search ................ 562/414, 562/409, 417, 485
See application file for complete search history.

(56) References Cited

U.S. PATENT DOCUMENTS

| | | | | |
|---|---|---|---|---|
| 5,354,898 A | * | 10/1994 | Schroeder | ............... 562/485 |
| 5,362,908 A | * | 11/1994 | Schroeder et al. | ........... 562/487 |
| 5,756,833 A | * | 5/1998 | Rosen et al. | ................ 562/486 |
| 2002/0002303 A1 | * | 1/2002 | Rosen | ........................ 562/414 |

FOREIGN PATENT DOCUMENTS

| | | | |
|---|---|---|---|
| JP | 07-149690 | * | 6/1995 |
| JP | 09-151162 | * | 6/1997 |
| JP | 2000-001456 | * | 1/2000 |

* cited by examiner

Primary Examiner—Taylor Victor Oh
(74) Attorney, Agent, or Firm—Antonelli, Terry, Stout & Kraus, LLP.

(57) ABSTRACT

A process for producing a high purity aromatic polycarboxylic acid (APA) by purification of a crude APA comprises: (I) aging a slurry of the crude APA in a first dispersion medium at 180 to 300° C. for 10 minutes or longer under stirring; (II) introducing the aged slurry of the APA into a column for substituting dispersion media, bringing the slurry into contact with a second dispersion medium and separating the resultant fluid into a fluid of the first dispersion medium containing impurities and a slurry of the second dispersion medium containing crystals of the high purity APA; and (III) separating the crystals of the high purity APA from the slurry of the second dispersion medium. A high purity APA having excellent hue and particle diameter can be industrially advantageously produced while the construction of the process is simplified and the consumption of energy is decreased.

20 Claims, 1 Drawing Sheet

PROCESS FOR PRODUCING A HIGH PURITY AROMATIC POLYCARBOXYLIC ACID

TECHNICAL FIELD

The present invention relates to a process for producing a high purity aromatic polycarboxylic acid which is useful as the raw material for polyesters, polyimides and liquid crystalline polymers, more particularly, to a process for industrially advantageously producing a high purity aromatic polycarboxylic acid having excellent hue and particle diameter while the construction of the process is simplified and the consumption of energy is decreased, and still more particularly, to a process for producing a high purity naphthalenepolycarboxylic acid and a high purity biphenylpolycarboxylic acid which are not easily purified.

BACKGROUND ART

Aromatic polycarboxylic acids are commercially important substances as chemical intermediates and have a wide demand as materials of polyesters, polyamides, polyimides and liquid crystalline polymers which are used for fibers, bottles, films and electronic applications. Examples of the aromatic polycarboxylic acids industrially used in the wide range of applications include terephthalic acid, isophthalic acid, phthalic acid, trimellitic acid, pyromellitic acid, 2,6-naphthalenedicarboxylic acid, 4,4'-biphenyldicarboxylic acid, 1,4,5,8-naphthalenetetracarboxylic acid and 3,3',4,4'-biphenyltetracarboxylic acid.

As the process for producing the aromatic polycarboxylic acid, processes in which an aromatic polyalkylhydrocarbon such as a xylene, a dialkylnaphthalene, a dialkylbiphenyl, a tetraalkylnaphthalene and a tetraalkylbiphenyl is oxidized with molecular oxygen at a high temperature under a high pressure in the presence of a heavy metal such as Co and Mn and a bromine compound in acetic acid as the solvent or oxidized with the air in the presence of nitric acid or chromic acid, are known. The aromatic polycarboxylic acid obtained by the oxidation reaction contains impurities such as monocarboxylic acids and aldehydes which are intermediate products of the oxidation reaction, addition products of bromine and metal components which are derived from the catalyst, and coloring substances having unknown structures.

When the aromatic polycarboxylic acid containing impurities is used as the material in the polymerization with a diol or a diamine, the obtained resin exhibits inferior physical and mechanical properties such as inferior heat resistance, mechanical strength and dimensional stability. Therefore, the aromatic polycarboxylic acid containing impurities cannot be used as the materials for polyesters, polyamides and polyimides. In general, crude aromatic polycarboxylic acids obtained by oxidation are colored yellow or black and cannot be used for applications requiring transparency such as bottles and films without further treatments. Moreover, since particles of crude aromatic polycarboxylic acids have, in general, small diameters, handling is not easy, and problems tend to arise during polymerization. Therefore, the process for industrially advantageously producing a high purity aromatic polycarboxylic acids having improved hue and particle diameter has been studied for a long time.

For example, in Japanese Patent Application Laid-Open No. Heisei 7(1995)-149690, a process in which a p-phenylene compound is oxidized in the liquid phase, the product is catalytically hydrogenated in water at a high temperature, the obtained slurry of terephthalic acid is introduced into a column for substituting solvents and brought into contact with an upward stream of water at a high temperature which is introduced at a lower portion of the column for substituting solvents, crystals of terephthalic acid are taken out of the bottom portion of the column as a slurry together with water at a high temperature, and crystal of a high purity terephthalic acid are separated, is described as the process for producing a high purity terephthalic acid.

In WO 02/088066, a process in which a crude aromatic polycarboxylic acid is formed into a slurry in an aqueous medium and brought into contact with a metal catalyst in the absence of oxygen while contamination of crystals with the catalyst components is prevented, is described.

In Japanese Patent Application Laid-Open No. Heisei 9(1997)-151162, a process in which a crude naphthalenedicarboxylic acid is dissolved into water at a high temperature under a high pressure, treated by reduction in the presence of a hydrogenation catalyst and then washed with a lower aliphatic carboxylic acid, is described. In U.S. Patent Application Laid-Open No. 2002/0002303, a process in which a crude naphthalenedicarboxylic acid is brought into contact with a metal of the Group VIII in the presence of hydrogen, is described.

In general, the purification of an organic compound is conducted in accordance with the process of distillation, crystallization or adsorption or a combination of these processes. However, since an aromatic polycarboxylic acid has a temperature of self-decomposition lower than the boiling point, the purification by distillation is substantially impossible. Since the solubility of an aromatic polycarboxylic acid in industrially widely used solvents is small, it is difficult that the easy purification by crystallization is conducted. In particular, naphthalenepolycarboxylic acids and biphenylpolycarboxylic acids are not easily dissolved in various solvents, and no industrially advantageous processes for producing high purity naphthalenepolycarboxylic acids and high purity biphenylpolycarboxylic acids have been established.

In the process in which an aromatic polycarboxylic acid is purified by completely dissolving the acid, a great amount of steam is necessary, and the cost of the utility is excessively great. In the processes for purifying an aromatic polycarboxylic acids described above, the acid is purified using a slurry having an increased concentration to decrease the consumption of energy. However, it is difficult that crystals of a high purity aromatic polycarboxylic acid having excellent hue and particle diameter are obtained in accordance with these processes.

The present invention has an object of providing a process for industrially advantageously producing an aromatic polycarboxylic acid having excellent hue and particle diameter while the construction of the process is simplified and the consumption of energy is decreased.

DISCLOSURE OF THE INVENTION

As the result of intensive studies by the present inventors to overcome the above problems, it was found that the quality of solid components (crystals) in a slurry was improved when the slurry in which a crude aromatic polycarboxylic acid was partially dissolved was aged under heating with stirring, a slurry containing crystals having the improved quality could be obtained by substituting the mother liquor of the slurry with a fresh dispersion medium, crystals of a high purity aromatic polycarboxylic acid having a great particle diameter could be obtained by separating the obtained crystals from the fluid while the construction of the process is industrially simplified, and thus the high purity aromatic polycarboxylic acid could be industrially advantageously produced. The present invention was completed based on this knowledge.

The present invention provides a process for producing a high purity aromatic polycarboxylic acid by purifying a crude aromatic polycarboxylic acid, which comprises:

(I), in a step of aging, aging a slurry comprising the crude aromatic polycarboxylic acid in a first dispersion medium under heating at 180 to 300° C. for 10 minutes or longer while being stirred;

(II), in a step of substituting dispersion media, introducing the slurry comprising the aromatic polycarboxylic acid which has been treated by aging under heating into a column for substituting dispersion media, bringing the slurry into contact with a second dispersion medium and separating a resultant fluid into a fluid of the first dispersion medium comprising impurities and a slurry of the second dispersion medium comprising crystals of the aromatic polycarboxylic acid; and (III), in a step of separating crystals, separating the crystals of the aromatic polycarboxylic acid from the slurry of the second dispersion medium.

THE MOST PREFERRED EMBODIMENT TO CARRY OUT THE INVENTION

Figure 1:
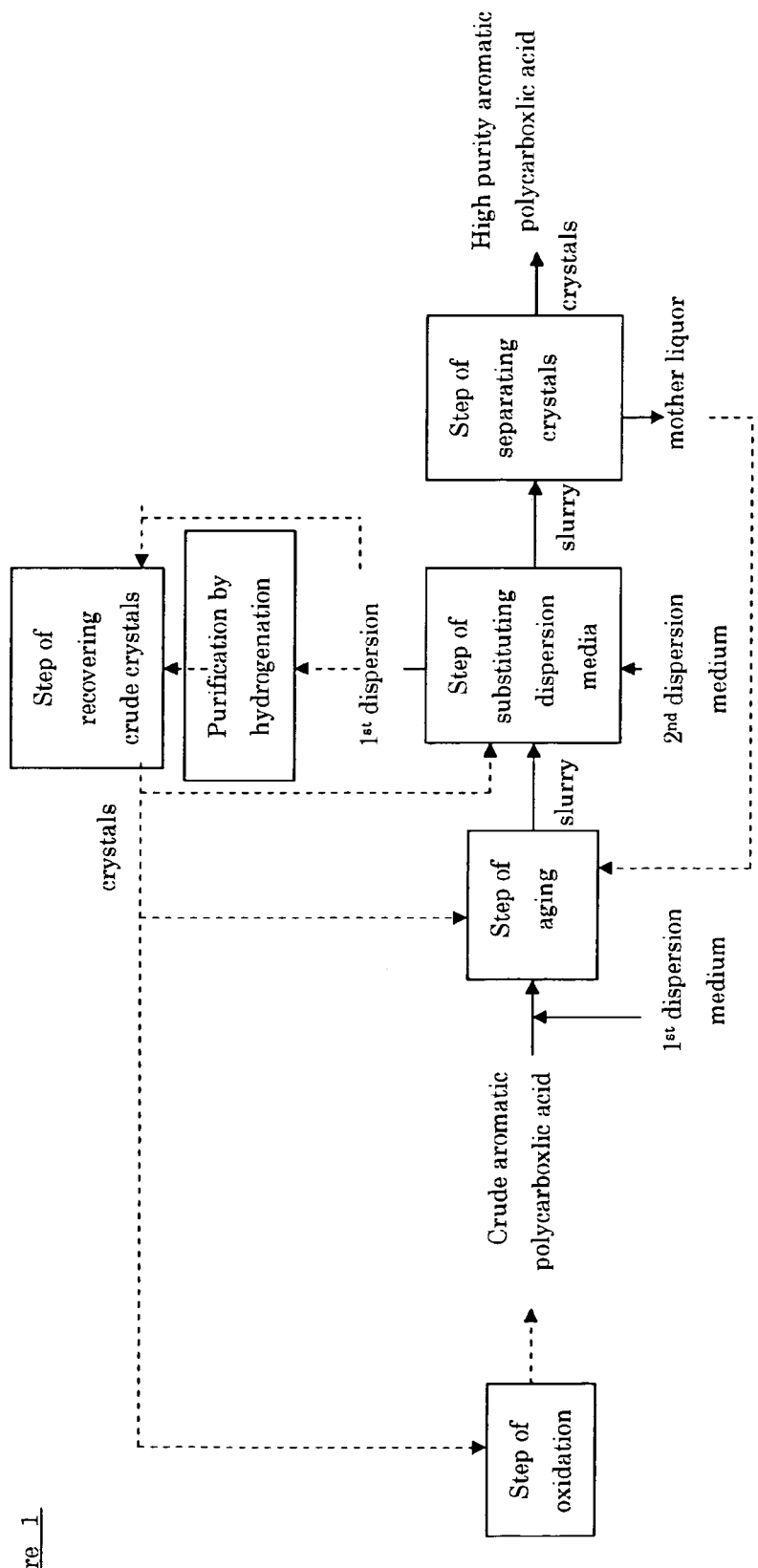
FIG. 1 shows a diagram exhibiting an example of the flow in the process for producing a high purity aromatic polycarboxylic acid of the present invention.

In the present invention, the process comprises (I) a step of aging, (II) a step of substituting dispersion media and (III) a step of separating crystals. FIG. 1 shows a diagram exhibiting an example of the flow of the process.

In FIG. 1, a crude aromatic polycarboxylic acid is produced by oxidation of a polyalkylaromatic compound used as the raw material for the aromatic polycarboxylic acid in the step of oxidation.

In the step of aging, a slurry in a dispersion medium (the first dispersion medium) is formed from crystals of the crude aromatic polycarboxylic acid obtained in the step of oxidation and aged under heating. In the step of substituting dispersion media, the slurry of the crude aromatic polycarboxylic acid taken out of the step of aging (a slurry of the first dispersion medium) is brought into contact with a fresh dispersion medium (a second dispersion medium) so that the substitution between the media is conducted continuously, and a slurry containing crystals and the fresh dispersion medium (a slurry of the second dispersion medium) and a fluid of the first dispersion medium containing impurities are obtained. In the step of separating crystals, crystals of the high purity aromatic polycarboxylic acid having an increased purity are separated from the slurry of the second dispersion medium.

As will be described later, the fluid of the first dispersion medium containing impurities which is obtained in the step of substituting dispersion media can be recycled into the step of oxidation, the step of aging or the step of substituting dispersion media after purification by hydrogenation, where necessary, and separation of crystals.

The aromatic polycarboxylic acid in the present invention is a compound in which at least two carboxyl groups are bonded to an aromatic hydrocarbon having at least one aromatic ring such as benzene, naphthalene and biphenyl. The process for producing the crude aromatic polycarboxylic acid used for the purification is not particularly limited. In general, the crude aromatic polycarboxylic acid can be obtained by oxidation of, as the raw material, a derivative of the aromatic hydrocarbon described above which is substituted with a polyfunctional groups giving carboxyl groups by oxidization, for example, an alkyl group such as methyl group, ethyl group and isopropyl group, formyl group and acetyl group. As described above, in general, the aromatic polycarboxylic acid has a temperature of self-decomposition lower than the boiling point, and the purification by distillation is substantially impossible. Since the solubility of the aromatic polycarboxylic acid in industrially widely used solvents is small, it is difficult that the easy purification by crystallization is conducted. The process of the present invention can be advantageously applied to purification of naphthalenepolycarboxylic acids and biphenylpolycarboxylic acids which are not easily soluble in various solvents.

Examples of the naphthalenepolycarboxylic acid include naphthalenedicarboxylic acids, naphthalenetricarboxylic acids and naphthalenetetracarboxylic acids. Among these compounds, naphthalenedicarboxylic acids which are useful as the raw material of polyesters, urethanes and liquid crystalline polymers are preferable, and 2,6-naphthalenedicarboxylic acid is more preferable. The naphthalenedicarboxylic acid can be obtained by oxidation of a dialkylnaphthalene with the molecular oxygen in the presence of an oxidation catalyst. The crude naphthalenedicarboxylic acid thus obtained contains coloring substances, metals of the oxidation catalyst and organic impurities such as formylnaphthoic acid which is an intermediate product of the oxidation reaction, trimellitic acid formed by decomposition of the naphthalene ring, naphthalenedicarboxylic bromide formed by addition of bromine and naphthalenetricarboxylic acid.

Examples of the biphenylpolycarboxylic acid include biphenyldicarboxylic acids, biphenyltricarboxylic acids and biphenyltetracarboxylic acids. Among these compounds, biphenyldicarboxylic acids which are useful as the raw material of polyesters, polyamides and liquid crystalline polymers are preferable, and 4,4'-biphenyldicarboxylic acid is more preferable. The biphenyldicarboxylic acid is obtained by oxidation of a dialkylbiphenyl with molecular oxygen in the presence of an oxidation catalyst. The crude biphenyldicarboxylic acid thus obtained contains coloring substances, metals of the oxidation catalyst and organic impurities such as formylbiphenylcarboxylic acid which is an intermediate product of the oxidation, alkylbiphenylcarboxylic acids and biphenylmonocarboxylic acid derived from the raw material.

(I) The Step of Aging

The crystals of the crude aromatic polycarboxylic acid contain impurities such as monocarboxylic acids and aldehydes which are intermediate products of the oxidation reaction, addition products of bromine and metal components which are derived from the catalyst and coloring substances having unknown structures, as described in BACKGROUND ART. In the step of aging, a slurry of the crystals of the crude aromatic polycarboxylic acid containing the impurities is formed in the first dispersion medium, and the impurities are transferred to or converted in the first dispersion medium to improve the quality of the crystals by aging the slurry under heating at a prescribed temperature with stirring. The stirring may be mechanical stirring or stirring with a gas. The mechanical stirring may be conducted using a stirrer in the aging tank or using a circulation pump.

As the first dispersion medium, water and/or acetic acid is preferable. The concentration of the slurry is not particularly limited as long as a portion of the aromatic polycarboxylic acid is dissolved and the slurry can be transferred by an ordinary industrial means. Since the diameter of particles obtained after the heat treatment does not depend on the concentration of the slurry, it is preferable that the concentration of the slurry is as great as possible from the standpoint of the efficiency of transfer.

The temperature of aging under heating depends on the type of the aromatic polycarboxylic acid to a great degree. With the consideration on the solubility of the crystals, the temperature is selected so as to achieve a rapid exchange of the dissolved aromatic polycarboxylic acid and the aromatic polycarboxylic acid not dissolved at the temperature of the treatment. The temperature is, in general, selected in the range of 180 to 300° C. and preferably in the range of 210 to 290° C. The higher the temperature of heating, the smaller the specific surface area of the aromatic polycarboxylic acid obtained finally, i.e., after the heating for a long time, and the greater the average particle diameter based on the specific surface area. When the temperature of heating is excessively low, the solubility of the crystals is small, and the residence time necessary for reaching the solid-liquid equilibrium becomes great. This causes an economic disadvantage.

In the present invention, the residence time in the aging tank is 10 minutes or longer and preferably 30 minutes or longer although the residence time depends on the type of the used aromatic polycarboxylic acid to a great degree. For obtaining the sufficient effect of the purification, the time required for reaching the solid-liquid equilibrium where no exchange of materials is apparently taking place between the dissolved aromatic polycarboxylic acid and the aromatic polycarboxylic acid not dissolved at the temperature of the treatment, is selected as the residence time. However, even when the slurry of the aromatic polycarboxylic acid is transferred from the aging tank to the column for substituting dispersion media at a shorter residence time before the solid-liquid equilibrium is achieved, the excellent effect of the purification can be exhibited. The necessary residence time is, in general, in the range of about 10 to 180 minutes although the necessary residence time is different depending on the particle diameter of the crude aromatic polycarboxylic acid.

In the process of the present invention, an atmosphere in which oxygen is substantially absent is preferable as the atmosphere of heating the slurry of the crude aromatic polycarboxylic acid. An inert gas such as the air or a gas containing the molecular hydrogen can be used. It is also possible that decarbonylation or hydrogenation is conducted in the presence of a catalyst. The partial pressure of hydrogen in the gas of the atmosphere is selected so as to prevent side reactions such as hydrogenation of nuclei at the temperature of the treatment. As the catalyst for the decarbonylation or the hydrogenation, catalysts supported noble metals such as platinum, palladium, ruthenium, rhodium, osmium, iridium and rhenium or metal components such as cobalt and nickel can be used. As the support, active carbon which is resistant to the fluid containing the aromatic polycarboxylic acid at a high temperature is preferable.

In the step of aging, coloring substances and organic impurities contained in the crude aromatic polycarboxylic acid are changed and distributed into the dispersion medium by aging under heating while the slurry of the crystals of the crude aromatic polycarboxylic acid is stirred or by conducting the decarbonylation or the hydrogenation in the presence of the catalyst. Metal components contained in the crude aromatic polycarboxylic acid can also be distributed into the dispersion medium. The diameter of the crystals of the aromatic polycarboxylic acid can be increased by maintaining the residence time at the prescribed temperature.

(II) The Step of Substituting Dispersion Media

In the step of substituting dispersion media, the slurry of the crude aromatic polycarboxylic acid taken out of the step of aging (the slurry of the first dispersion medium) is brought into contact with a fresh dispersion medium (the second dispersion medium), and a slurry comprising the crystals and the fresh dispersion medium (the slurry of the second dispersion medium) is obtained by the continuous substitution of the dispersion media. In the step of substituting dispersion media (II), a vertical column for substituting dispersion media is preferably used. It is preferable that the slurry of the first dispersion medium is supplied from a portion around the top of the column while the condition obtained from the aging tank is maintained without change, and the second dispersion medium is supplied from a lower portion of the column for substituting dispersion media.

As the second dispersion medium introduced into the column for substituting media, water and/or acetic acid is preferable. It is preferable that the temperature of the second dispersion medium introduced into the column for substituting dispersion media is lower than the temperature of the slurry containing the aromatic polycarboxylic acid which is introduced into the column for substituting dispersion media.

To increase the efficiency in the step of separation of crystals (III), it is preferable that the concentration of the aromatic polycarboxylic acid in the slurry of the aromatic polycarboxylic acid taken out of the bottom portion of the column for substituting dispersion media (the slurry of the second dispersion medium) is greater than the concentration of the aromatic polycarboxylic acid in the slurry of the aromatic polycarboxylic acid introduced into the column for substituting dispersion media (the slurry of the first dispersion medium).

(III) The Step of Separating Crystals

In the step of separating crystals, the crystals of the aromatic polycarboxylic acid are separated by crystallization and filtration from the slurry of the second dispersion medium obtained in the step of substituting dispersion media. Due to this operation, the high purity aromatic polycarboxylic acid having the increased purity can be obtained. It is possible that the mother liquor (the filtrate) separated from the crystals is recycled into the step of aging.

(IV) The Step of Recovering Crude Crystals

In the present invention, as shown in FIG. 1, the fluid of the first dispersion medium taken out in the step of substituting dispersion media and containing impurities can be treated for separation of crystals by lowering the pressure or the temperature without further treatments or, where necessary, after purification by hydrogenation or decarbonylation in the presence of a catalyst, and the obtained crystals can be recycled into the step of aging, the step of substituting dispersion media or the step of oxidation (the step of producing the crude aromatic polycarboxylic acid).

As the catalyst used for the purification by hydrogenation, any catalyst may be used as long as the catalyst exhibits the activity for hydrogenation in the condition of the purification and is not easily degraded. As the support which is resistant to the fluid containing the aromatic polycarboxylic acid at a high temperature, active carbon or titania is preferable. As the supported metal, metals of the Group VIII are preferable, and noble metals such as palladium and platinum are more preferable. It is preferable that the temperature of the purification by hydrogenation is the same as the temperature at the column for substituting dispersion media. The partial pressure of hydrogen in the purification by hydrogenation is selected suitably so that hydrogenation of the nuclei of the aromatic polycarboxylic acid does not take place and the substances adversely affecting the polymerization and substances causing coloring are efficiently hydrogenated although the partial pressure is different depending on the aromatic polycarboxylic acid.

As clearly shown in the following examples, in accordance with the process of the present invention, the high purity aromatic polycarboxylic acid having a great particle diameter and excellent quality can be obtained from the crude aromatic polycarboxylic acid while the construction of the process is simplified. By the recycling of the crystals in the dispersion medium in combination with the purification by hydrogenation, the high purity aromatic polycarboxylic acid can be easily obtained at a great yield.

In other words, in accordance with the present invention, the crystals of the high purity aromatic polycarboxylic acid can be separated from coloring substances, organic impurities and metal components contained in the crystals of the crude aromatic polycarboxylic acid by the treatments in the above steps. In the present invention, by using the column for substituting dispersion media, the apparatus for the reaction is made smaller and simpler, the crystals of the aromatic polycarboxylic acid having a great particle diameter and an excellent quality can be easily produced, and the consumption of energy in the purification step can be remarkably decreased.

Therefore, the high purity aromatic polycarboxylic acid can be industrially advantageously produced in accordance with the process of the present invention. The advantages exhibited by the present invention are remarkably great.

EXAMPLES

The present invention will be described more specifically with reference to examples in the following. However, the present invention is not limited to the examples.

In Examples and Comparative Example described in the following, organic impurities in crystals of a crude aromatic polycarboxylic acid used as the raw material and a high purity aromatic polycarboxylic acid were analyzed in accordance with the gas chromatography after converting the acid into the methyl ester. For the evaluation of the hue, 1 g of a sample was dissolved into 10 ml of an aqueous solution of sodium hydroxide, and the hue was evaluated based on the absorbance of light of 400 nm (referred to as $OD_{400}$, hereinafter) using a quartz cell of 10 mm. The value of $OD_{400}$ reflects the amounts of colored impurities and substances causing coloring in the aromatic polycarboxylic acid. The smaller the value of $OD_{400}$, the smaller the amounts of colored and coloring impurities. The average particle diameter was measured using a dry-type meter of the distribution of the particle diameter of the laser diffraction type (HORIBA LA-500).

Example 1

(I) Step of Aging

Crystals of a crude 2,6-naphthalenedicarboxylic acid (the content of formylnaphthoic acid: 2,500 ppm; $OD_{400}$: 1.5; the average particle diameter of the crystals: 5 μm) which was obtained by oxidation of 2,6-dimethylnaphthalene in the liquid phase in the presence of a Co/Mn/Br-based catalyst was mixed with water to prepare a slurry having a concentration of 20% by weight, and 300 g of the obtained slurry was placed into a 500 ml autoclave equipped with a stirrer under an atmosphere of nitrogen and heated at 280° C. Then, crystals of a crude 2,6-naphthalenedicarboxylic acid similar to the material used above was mixed with water to prepare a slurry having a concentration of 20% by weight, and the prepared slurry was supplied continuously into the autoclave at a rate of 120 g/hour at the room temperature. The residence time in the aging tank at 280° C. was kept at 3 hours, and a slurry was continuously taken out of the bottom portion of the autoclave at a rate of 120 g/hour. The crystals of 2,6-naphthalenedicarboxylic acid taken out of the bottom portion of the autoclave had an average particle diameter of 50 μm. The solubility of 2,6-naphthalenedicarboxylic acid in water at 280° C. is about 6 g in 100 g of water.

(II) Step of Substituting Dispersion Media

The slurry containing 2,6-naphthalenedicarboxylic acid which was taken out of the bottom portion of the autoclave was supplied to an upper portion of a column for substituting dispersion media having a diameter of 25 mmϕ and a height of 50 cm at 280° C. at a rate of 120 g/hour without further treatments. Water at 90° C. was supplied at a lower portion of the column for substituting dispersion media at a rate of 100 g/hour. A fluid at the top of the column was taken out at a rate of 100 g/hour, and a slurry containing crystals of 2,6-naphthalenedicarboxylic acid was taken out of the bottom portion of the column at a rate of 120 g/hour.

(III) Step of Separating Crystals

Crystals of 2,6-naphthalenedicarboxylic acid was separated from the slurry containing 2,6-naphthalenedicarboxylic acid taken out of the bottom portion of the column for replacing dispersion medium under the ordinary pressure by filtration. The obtained crystals were rinsed with water at 90° C. and then dried. The obtained crystals of high purity 2,6-naphthalenedicarboxylic acid had a content of formylnaphthoic acid of 10 ppm or smaller, an $OD_{400}$ of 0.09 and an average particle diameter of crystals of 40 μm. The obtained 2,6-naphthalenedicarboxylic acid was polycondensed with ethylene glycol, and a polyester was obtained. Pellets of the obtained polyester were colorless and transparent.

Example 2

The same procedures as those conducted in Example 1 were conducted except that a crude 4,4'-biphenyldicarboxylic acid containing 3,000 ppm of formylbiphenylcarboxylic acid and having an $OD_{400}$ of 1.6 and an average particle diameter of crystals of 4 μm was used in place of the crude 2,6-naphthalenedicarboxylic acid in (I) Step of aging of Example 1. The obtained crystals of high purity 4,4'-biphenyldicarboxylic acid had a content of formylbiphenylcarboxylic acid of 10 ppm or smaller, an $OD_{400}$ of 0.08 and an average particle diameter of crystals of 50 μm. The obtained 4,4'-biphenyldicarboxylic acid was polycondensed with ethylene glycol, and a polyester was obtained. Pellets of the obtained polyester were colorless and transparent.

Example 3

The same procedures as those conducted in Example 1 were conducted except that the residence time in the aging tank was 10 minutes in (I) Step of aging of Example 1. The obtained crystals of high purity 2,6-naphthalenedicarboxylic acid had a content of formylnaphthoic acid of 1,000 ppm, an $OD_{400}$ of 0.9 and an average particle diameter of crystals of 16 μm. The obtained 2,6-naphthalenedicarboxylic acid was polycondensed with ethylene glycol, and a polyester was obtained. Pellets of the obtained polyester were slightly colored.

Example 4

The same procedures as those conducted in Example 1 were conducted except that the residence time in the aging tank was 30 minutes in (I) Step of aging of Example 1. The obtained crystals of high purity 2,6-naphthalenedicarboxylic acid had a content of formylnaphthoic acid of 100 ppm, an $OD_{400}$ of 0.2 and an average particle diameter of crystals of 30 µm. The obtained 2,6-naphthalenedicarboxylic acid was polycondensed with ethylene glycol, and a polyester was obtained. Pellets of the obtained polyester were slightly colored.

Comparative Example 1

The same procedures as those conducted in Example 1 were conducted except that the residence time in the aging tank was 5 minutes in (I) Step of aging of Example 1. The obtained crystals of high purity 2,6-naphthalenedicarboxylic acid had a content of formylnaphthoic acid of 2,000 ppm, an $OD_{400}$ of 1.2 and an average particle diameter of crystals of 10 µm. The obtained 2,6-naphthalenedicarboxylic acid was polycondensed with ethylene glycol, and a polyester was obtained. Pellets of the obtained polyester were slightly colored.

Comparative Example 2

The same procedures as those conducted in Example 1 were conducted except that the temperature of the aging tank was 160° C. in (I) Step of aging of Example 1. The obtained crystals of high purity 2,6-naphthalenedicarboxylic acid had a content of formylnaphthoic acid of 2,300 ppm, an $OD_{400}$ of 1.3 and an average particle diameter of crystals of 7 µm. The obtained 2,6-naphthalenedicarboxylic acid was polycondensed with ethylene glycol, and a polyester was obtained. Pellets of the obtained polyester were slightly colored.

Comparative Example 3

Among the steps conducted in Example 1, the step of aging alone was conducted for the purification without conducting the step of substituting dispersion media and the steps thereafter. Specifically, the pressure of the slurry obtained in step of aging (I) was lowered to the ordinary pressure, and the obtained crystals were separated by filtration, rinsed with water at 90° C. and dried. The obtained crystals of high purity 2,6-naphthalenedicarboxylic acid had a content of formylnaphthoic acid of 2,000 ppm or greater, an $OD_{400}$ of 1.35 and an average particle diameter of crystals of 40 µm. The obtained 2,6-naphthalenedicarboxylic acid was polycondensed with ethylene glycol, and a polyester was obtained. Pellets of the obtained polyester were slightly colored.

Example 5

Into a column for hydrogenation packed with 100 ml of active carbon of coconut husk supporting 0.5% by weight of Pd, the fluid obtained at the top of the column for substituting dispersion media in (II) Step of substituting dispersion media of Example 1 was supplied while the temperature was kept at 280° C., and the hydrogenation was conducted under a partial pressure of hydrogen of 0.2 MPa. Then, the pressure was reduced to the ordinary pressure, and the obtained crystals were separated by filtration. The obtained crystals of 2,6-naphthalenedicarboxylic acid had a content of formylnaphthoic acid of 20 ppm or smaller and an $OD_{400}$ of 0.6. The crystals of the recovered 2,6-naphthalenedicarboxylic acid in an amount corresponding to 20% by weight of the supplied crude 2,6-naphthalenedicarboxylic acid were recycled to (I) Step of aging. The same procedures as those conducted in Example 1 were conducted except the procedures described above. Crystals of high purity 2,6-naphthalenedicarboxylic acid obtained after (III) Step of separation of crystals had a content of formylnaphthoic acid of 10 ppm or smaller, an $OD_{400}$ of 0.07 and an average particle diameter of crystals of 40 µm. The obtained 2,6-naphthalenedicarboxylic acid was polycondensed with ethylene glycol, and a polyester was obtained. Pellets of the obtained polyester were colorless and transparent.

Example 6

Into a column for hydrogenation packed with 100 ml of active carbon of coconut husk supporting 0.5% by weight of Pd, the fluid obtained at the top of the column for substituting dispersion media in (II) Step of substituting dispersion media of Example 1 was supplied while the temperature was kept at 280° C., and the hydrogenation was conducted under a partial pressure of hydrogen of 0.2 MPa. Then, the pressure was reduced to the ordinary pressure, and the obtained crystals were separated by filtration. The obtained crystals of 2,6-naphthalenedicarboxylic acid had a content of formylnaphthoic acid of 20 ppm or smaller and an $OD_{400}$ of 0.6. The crystals of the recovered 2,6-naphthalenedicarboxylic acid in an amount corresponding to 20% by weight of the supplied crude 2,6-naphthalenedicarboxylic acid was recycled to (II) Step of substituting dispersion media. The same procedures as those conducted in Example 1 were conducted except the procedures described above. Crystals of high purity 2,6-naphthalenedicarboxylic acid obtained after (III) Step of separation of crystals had a content of formylnaphthoic acid of 10 ppm or smaller, an $OD_{400}$ of 0.07 and an average particle diameter of crystals of 40 µm. The obtained 2,6-naphthalenedicarboxylic acid was polycondensed with ethylene glycol, and a polyester was obtained. Pellets of the obtained polyester were colorless and transparent.

Example 7

The same procedures as those conducted in Example 1 were conducted except that 50 ml of active carbon of coconut husk supporting 0.5% by weight of Pd was packed into a net made of a metal and placed into the aging tank in (I) Step of aging of Example 1. Crystals of high purity 2,6-naphthalenedicarboxylic acid obtained after (III) Step of separation of crystals had a content of formylnaphthoic acid of 10 ppm or smaller, an $OD_{400}$ of 0.08 and an average particle diameter of crystals of 50 µm. The obtained 2,6-naphthalenedicarboxylic acid was polycondensed with ethylene glycol, and a polyester was obtained. Pellets of the obtained polyester were slightly colorless and transparent.

Example 8

In (II) Step of substituting dispersion media of Example 1, the slurry containing 2,6-naphthalenedicarboxylic acid taken out of the bottom portion of the autoclave of the aging tank was supplied without further treatments to an upper portion of the column for substituting dispersion media having a diameter of 25 mmφ and a height of 50 cm at a rate of 120 g/hour while the temperature was kept at 280° C. Water at 90° C. was supplied from the bottom portion of the column for substituting dispersion media at a rate of 80 g/hour. The fluid at the top of the column was taken out at a rate of 100 g/hour, and a slurry containing crystals of 2,6-naphthalenedicarboxylic acid was taken out of the bottom portion of the column at a rate of 100 g/hour. The same procedures as those conducted in Example 1 were conducted except the procedures described above. Crystals of high purity 2,6-naphthalenedicarboxylic acid obtained after (III) Step of separation of crystals had a content of formylnaphthoic acid of 10 ppm or smaller, an $OD_{400}$ of 0.09 and an average particle diameter of crystals of 40 μm. The obtained 2,6-naphthalenedicarboxylic acid was polycondensed with ethylene glycol, and a polyester was obtained. Pellets of the obtained polyester were colorless and transparent.

From the above Examples, the following results were confirmed:

1) The particle diameter was increased, and organic impurities were distributed into the dispersion medium by aging the slurry containing the crude aromatic polycarboxylic acid under heating at the high temperature.

2) The high purity aromatic polycarboxylic acid was obtained at the bottom portion of the column for substituting dispersion media when the slurry containing the crude aromatic polycarboxylic acid which had been aged under heating at the high temperature was supplied to the column.

3) The aromatic polycarboxylic acid having a greater purity than that of the crude aromatic polycarboxylic acid could be obtained by purifying the first dispersion medium containing impurities, which was obtained at the top portion of the column for substituting dispersion media, by hydrogenation. The efficiency of production in the purification of the crude aromatic polycarboxylic acid was improved by recycling the above aromatic polycarboxylic acid having the improved purity.

The invention claimed is:

1. A process for producing a high purity aromatic polycarboxylic acid selected from the group consisting of naphthalenepolycarboxylic acids and biphenylpolycarboxylic acids by purifying a crude aromatic polycarboxytic acid selected from the group consisting of crude naphthalenepolycarboxylic acids and crude biphenylpolycarboxylic acids, respectively, which comprises:

(I), in a step of aging, aging a slurry comprising the crude aromatic polycarboxylic acid in a first dispersion medium under heating at 210 to 290° C. for 10 minutes or longer while being stirred;

(II), in a step of substituting dispersion media, introducing the slurry comprising the aromatic polycarboxylic acid which has been treated by aging under heating into a column for substituting dispersion media, bringing the slurry into contact with a second dispersion medium and separating a resultant fluid into a fluid of the first dispersion medium and a slurry of the second dispersion medium comprising crystals of the aromatic polycarboxylic acid; and (III), in a step of separating crystals, separating the crystals of the aromatic polycarboxylic acid from the slurry of the second dispersion medium.

2. A process for producing a high purity aromatic polycarboxylic acid according to claim 1, wherein the first dispersion medium is at least one medium selected from water and acetic acid.

3. A process for producing a high purity aromatic polycarboxylic acid according to claim 1, wherein the second dispersion medium is at least one medium selected from the group consisting of water and acetic acid.

4. A process for producing a high purity aromatic polycarboxylic acid according to claim 1, wherein, in the step of aging (I), the treatment of aging under heating is conducted under an atmosphere of a gas comprising an inert gas or molecular hydrogen.

5. A process for producing a high purity aromatic polycarboxylic acid according to claim 4, wherein the treatment of aging under heating is conducted in a presence of a catalyst selected from the group consisting of platinum, palladium, ruthenium, rhodium, osmium, iridium, rhenium, cobalt and nickel.

6. A process for producing a high purity aromatic polycarboxylic acid according to claim 1, wherein, in the step of substituting dispersion media (II), a temperature of the second dispersion medium introduced into the column for substituting dispersion media is lower than a temperature of the slurry comprising the aromatic polycarboxylic acid which is introduced into the column for substituting dispersion media.

7. A process for producing a high purity aromatic polycarboxylic acid according to claim 1, wherein, in the step of substituting dispersion media (II), a concentration of the aromatic polycarboxylic acid in the slurry of the second dispersion medium which is separated in the column for substituting dispersion media is greater than a concentration of the aromatic polycarboxylic acid in the slurry comprising the aromatic polycarboxylic acid which is introduced into the column for substituting dispersion media.

8. A process for producing a high purity aromatic polycarboxylic acid according to claim 1, wherein the fluid of the first dispersion medium which is taken out in the step of substituting dispersion media II is purified by hydrogenation in a presence of a metal catalyst selected from the group consisting of platinum, palladium, ruthenium, rhodium, osmium, iridium, rhenium, cobalt and nickel, and crystals formed in the fluid are separated and used by recycling into the step of aging (I) or the step of substituting dispersion media (II).

9. A process for producing a high purity aromatic polycarboxylic acid according to claim 1, wherein the aromatic polycarboxylic acid is at least one compound selected from the group consisting of 2,6-naphthalenedicarboxylic acid and 4,4'-biphenyldicarboxylic acid.

10. A process for producing a high purity aromatic polycarboxylic acid according to claim 2, wherein the second dispersion medium is at least one medium selected from the group consisting of water and acetic acid.

11. A process for producing high purity aromatic polycarboxylic acid according to claim 1, wherein said fluid of the first dispersion medium, separated in the step of substituting dispersion medium, is recycled to an oxidation step for forming said crude aromatic polycarboxylic acid, said step for aging or said step of substituting dispersion media.

12. A process for producing high purity aromatic polycarboxylic acid according to claim 11, wherein said fluid of the first dispersion medium, separated in the step of substituting dispersion media, is recycled to said oxidation step.

13. A process for producing high purity aromatic polycarboxylic acid according to claim 1, wherein said naphthalenepolycarboxylic acid is selected from the group consisting of naphthalenedicarboxylic acid, naphthalenetricarboxylic acid and naphthalenetetracarboxylic acid, and said biphenylpolycarboxylic acid is selected from the group consisting of biphenyldicarboxylic acid, biphenyltricarboxylic acid and biphenyltetracarboxylic acid.

14. A process for producing high purity aromatic polycarboxylic acid according to claim 1, wherein said heating is performed for at least 30 minutes.

15. A process for producing high purity aromatic polycarboxylic acid according to claim 1, wherein in the step of substituting dispersion media, said slurry of the first dispersion medium is supplied around the top of the column, and the second dispersion medium is supplied to a lower portion of the column.

16. A process for producing high purity aromatic polycarboxylic acid according to claim 1, wherein said crude aromatic carboxylic acid includes impurities, and, in the step of substituting dispersion media, the resultant fluid is separated into a fluid of the first dispersion medium comprising impurities and the slurry of the second dispersion medium comprising crystals of the aromatic polycarboxylic acid.

17. A process for producing a high purity aromatic polycarboxylic acid according to claim 1, wherein said heating in the step of aging is at a temperature of 280 to 290° C.

18. A process for producing a high purity aromatic polycarboxylic acid according to claim 1, wherein said heating in the step of aging is performed for 10 to 180 minutes.

19. A process for producing a high purity aromatic polycarboxylic acid according to claim 14, wherein said heating in the step of aging is at a temperature of 280 to 290° C.

20. A process for producing a high purity aromatic polycarboxylic acid selected from the group consisting of naphthalenepolycarboxylic acids and biphenylpolycarboxylic acids by purifying a crude aromatic polycarboxylic acid selected from the group consisting of crude naphthalenepolycarboxylic acids and crude biphenylpolycarboxylic acids, respectively, which comprises:
   (I), in a step of aging, aging a slurry comprising the crude aromatic polycarboxylic acid in a first dispersion medium under heating at 280 to 300° C. for 10 minutes or longer while being stirred;
   (II), in a step of substituting dispersion media, introducing the slurry comprising the aromatic polycarboxylic acid which has been treated by aging under heating into a column for substituting dispersion media, bringing the slurry into contact with a second dispersion medium and separating a resultant fluid into a fluid of the first dispersion medium and a slurry of the second dispersion medium comprising crystals of the aromatic polycarboxylic acid; and
   (III), in a step of separating crystals, separating the crystals of the aromatic polycarboxylic acid from the slurry of the second dispersion medium.

* * * * *